US009095500B2

(12) United States Patent
Brandenburger et al.

(10) Patent No.: US 9,095,500 B2

(45) Date of Patent: Aug. 4, 2015

(54) CLOSURE CAP FOR A CONTAINER FOR RECEIVING MEDICAL LIQUIDS, AND CONTAINER FOR RECEIVING MEDICAL LIQUIDS

(75) Inventors: Torsten Brandenburger, Reichelsheim (DE); Gerhard Greier, Friedrichsdorf (DE)

(73) Assignee: Fresenius Kabi Deutschland GmgH, Bad Homburg v.d.H. (DE)

( * ) Notice: Subject to any disclaimer, the term of this patent is extended or adjusted under 35 U.S.C. 154(b) by 961 days.

(21) Appl. No.: 12/523,971

(22) PCT Filed: Feb. 4, 2008

(86) PCT No.: PCT/EP2008/000851

§ 371 (c)(1), (2), (4) Date: Jul. 21, 2009

(87) PCT Pub. No.: WO2008/095665

PCT Pub. Date: Aug. 14, 2008

(65) Prior Publication Data

US 2010/0059474 A1 Mar. 11, 2010

(30) Foreign Application Priority Data

Feb. 3, 2007 (DE) ......................... 10 2007 005 407

(51) Int. Cl.

*A61B 19/00* (2006.01)

*A61M 5/32* (2006.01)

(Continued)

(52) U.S. Cl.

CPC .............. *A61J 1/2096* (2013.01); *A61J 1/1412* (2013.01); *A61J 1/1418* (2015.05); *A61J 1/1431* (2015.05);

(Continued)

(58) Field of Classification Search

CPC ..... A61J 1/10; A61J 1/2096; A61J 2001/201; A61J 1/1406

USPC ........... 604/403–416; 215/316, 320, 341, 349

See application file for complete search history.

(56) References Cited

U.S. PATENT DOCUMENTS 5,135,489 A 8/1992 Jepson et al.

5,957,898 A * 9/1999 Jepson et al. ................. 604/256

(Continued)

FOREIGN PATENT DOCUMENTS

DE 20 2004 003 267 U1 5/2004

DE 103 48 016 A1 6/2005

(Continued)

OTHER PUBLICATIONS

The International Bureau of WIPO. PCT Notification of Transmittal of Translation of the International Preliminary Report on Patentability. Form PCT/IB/338. (1 page). Oct. 15, 2009.

(Continued)

*Primary Examiner* — Philip R Wiest

(74) *Attorney, Agent, or Firm* — Sterne, Kessler, Goldstein & Fox P.L.L.C.

(57) ABSTRACT

The invention relates to a closure cap for a container for receiving medical liquids, in particular a BFS vial which is produced by a blow-fill seal process, and to a BFS container with such a closure cap. The closure cap according to the invention has a cover part and an edge part, with an injection part arranged in the cover part. The injection part has an outwardly directed connection part with a conical recess for receiving the cone stem of a needleless injection syringe in a seal-forming manner, and an inwardly directed closure part which has a self-sealing membrane for closing the recess of the connection part. The self-sealing membrane is slotted. The closure cap according to the invention allows a liquid to be injected without use of an injection needle.

12 Claims, 4 Drawing Sheets

(51) Int. Cl.

| | |
|---|---|
| ***A61J 1/20*** | (2006.01) |
| ***A61J 1/14*** | (2006.01) |
| ***A61J 1/18*** | (2006.01) |
| *B65D 41/00* | (2006.01) |

(52) U.S. Cl.

CPC .. *A61J 1/18* (2013.01); *A61J 1/201* (2015.05); *A61J 1/2044* (2015.05); *A61J 2001/1418* (2013.01); *A61J 2001/1431* (2013.01); *A61J 2001/201* (2013.01); *A61J 2001/2044* (2013.01)

(56) References Cited

U.S. PATENT DOCUMENTS

| | | | | |
|---|---|---|---|---|
| 6,173,852 | B1 * | 1/2001 | Browne | 215/247 |
| 6,681,946 | B1 | 1/2004 | Jansen et al. | |
| 8,177,760 | B2 * | 5/2012 | Rome et al. | 604/247 |
| 2003/0075469 | A1 * | 4/2003 | Herbert | 206/438 |
| 2004/0068238 | A1 * | 4/2004 | Utterberg et al. | 604/256 |
| 2004/0112855 | A1 * | 6/2004 | Becker | 215/247 |
| 2004/0199126 | A1 * | 10/2004 | Harding et al. | 604/256 |
| 2006/0138070 | A1 * | 6/2006 | Domkowski et al. | 215/247 |
| 2007/0060902 | A1 | 3/2007 | Brandenburger et al. | |
| 2007/0106244 | A1 * | 5/2007 | Mosler et al. | 604/411 |
| 2009/0054865 | A1 | 2/2009 | Brandenburger et al. | |

FOREIGN PATENT DOCUMENTS

| | | | |
|---|---|---|---|
| DE | 10 2004 051 300 | B3 | 11/2005 |
| EP | 1 616 808 | A1 | 1/2006 |
| GB | 2 089 332 | A | 6/1982 |
| WO | WO 90/11103 | A2 | 10/1990 |
| WO | WO 9503841 | | 2/1995 |
| WO | WO 9623545 | A1 | 8/1996 |
| WO | WO 9937268 | | 7/1999 |
| WO | WO 2005/037362 | A1 | 4/2005 |
| WO | WO 2005037362 | A1 | 4/2005 |
| WO | WO 2006/042579 | A1 | 4/2006 |
| WO | WO 2006/060128 | A2 | 8/2006 |

OTHER PUBLICATIONS

The International Bureau of WIPO. PCT International Preliminary Report on Patentability—Chapter I. Form PCT/IB/373. (1 page). Oct. 6, 2009.

The International Bureau of WIPO. PCT Written Opinion of the International Searching Authority. Form PCT/ISA/237. English Language Translation. (3 pages). Jun. 2, 2008.

European Patent Office. PCT International Search Report. International Application No. PCT/EP2008/000851. International Filing Date: Apr. 2, 2008. German Language. 4 pages. Jun. 2, 2008.

* cited by examiner

Fig. 5
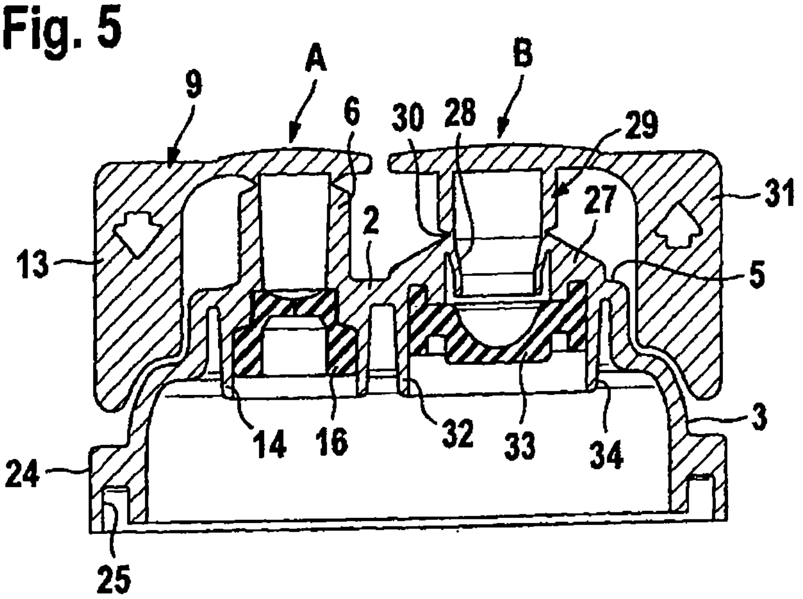
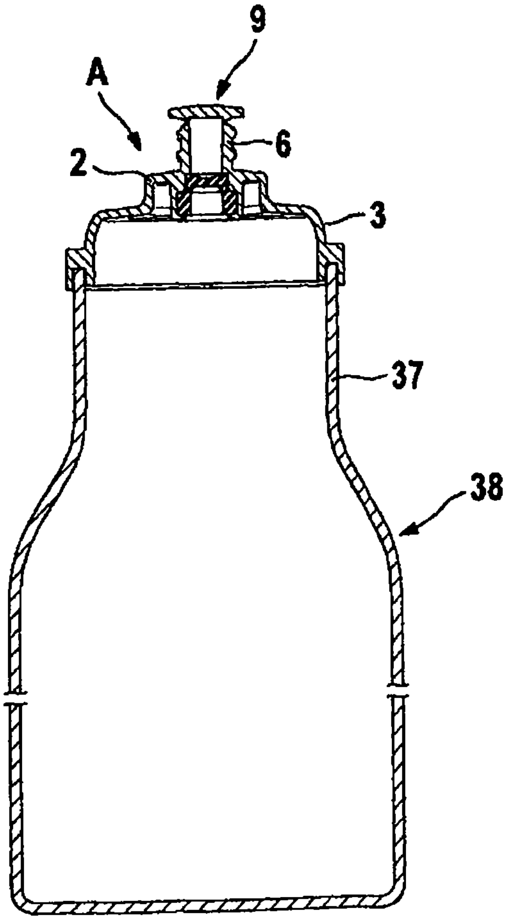
Fig. 6

CLOSURE CAP FOR A CONTAINER FOR RECEIVING MEDICAL LIQUIDS, AND CONTAINER FOR RECEIVING MEDICAL LIQUIDS

CROSS REFERENCES TO RELATED APPLICATIONS

This application is a U.S. National Stage entry of co-pending International Patent Application No. PCT/EP2008/000851 filed on Feb. 4, 2008 by BRANDENBURGER, Torsten et al. entitled CLOSURE CAP FOR A CONTAINER FOR RECEIVING MEDICAL LIQUIDS, AND CONTAINER FOR RECEIVING MEDICAL LIQUIDS, the entire contents of which is incorporated by reference, and for which priority is claimed under 35 U.S.C. §371. As in the parent International Application No. PCT/EP2008/000851, priority is also claimed to co-pending German Paten Application No. 10 2007 005 407.8 filed on Feb. 3, 2007, the entire contents of which is incorporated by reference for which priority is claimed under 35 U.S.C. §119.

BACKGROUND OF THE INVENTION

1. Field of the Invention

The invention relates to a closure cap for a container for receiving medical liquids, and in particular an infusion or transfusion container, which closure cap has a cover portion and a rim portion. As well as this, the invention also relates to a container for receiving medical liquids, and in particular a BFS container, which has a closure cap of this kind.

2. Background Art

There is a process, known as the blow-fill-seal process (BFS process), in which, in a single operation and sterilely and while remaining pyrogen-free, containers, such for example as bottles of extruded PE or PP, are blown to a desired shape and immediately on cooling are filled aseptically with a desired filling and are hermetically sealed. The containers, and in particular the bottles, which are produced by the blow-fill-seal process are also referred to as BFS containers.

When known BFS containers are used to receive sterile medical liquids, such for example as infusion solutions, they require a closure cap system which allows the infusion solution to be transferred to the patient by means of an infusion device. It should also be possible for medications to be added to the infusion solution.

Known from WO 96/23545 is an infusion bag which has an injection part and a withdrawal part. The withdrawal part is used to allow the infusion solution to be withdrawn by means of a spike, whereas the injection part is used to allow a medication to be fed in by means of an injection syringe which has a thin needle. The injection part comprises a tubular portion for connection which is closed off by a protective cap in the form of a break-off part. Seated in the portion for connection is a self-sealing membrane (septum) which is pierced by the needle of the injection syringe. A piercable membrane in the portion for connection stops the septum from coming into contact with the solution before the infusion bag is used. The withdrawal part does not have a self-sealing septum. The injection and withdrawal parts known from WO 96/23545 are intended to be welded into an infusion bag.

The known injection parts have proved satisfactory in practice. There are however disadvantages which arise from the use of an injection needle for injecting an active agent. On the one hand there is a risk of the connection between the injection needle and the septum becoming disconnected due to an unintentional pull on the syringe or a pressure above atmospheric inside the bag. On the other hand there is an increased risk of injury to the nursing staff due to the injection needle. The infusion bag into which the injection part is welded may also be damaged by the needle in the event of inexpert handling. As well as this, it is also more difficult for a viscous active agent to be fed in due to the small cross-section of the needle. In addition, it takes a relatively long time even to feed in an active agent of low viscosity due to the small cross-section of the needle.

For connecting up medical devices, there are in medical engineering known conical connectors with a conical tip and a conical socket whose conical surfaces are standardised. The non-lockable conical connectors having standardised conical surfaces are referred to as Luer connectors and the lockable conical connectors are referred to as Luer-lock connectors. Luer or Luer-lock connectors having a conical tip are referred to as male connectors and the connectors having conical sockets are referred to as female connectors.

DE 103 48 016 A1 describes a connector for welding into an infusion bag which allows an active agent to be injected by means of a conventional Luer-lock syringe which does not have an injection needle. The known connector has a portion for connection which has a recess in the form of a passage in which a self-sealing membrane is arranged. A break-off part which is connected to the portion for connection seals off the recess in passage form. Above the membrane, the portion for connection takes the form of a connecting piece having an internal cone and an outside thread, the membrane being slit to receive the conical tip of a syringe while forming a seal against it. The connector is made up of an upper sub-section and a lower sub-section between which the self-sealing membrane is held by a clamping action.

Known from DE 20 2004 003 267 U1 is a closure cap for a BFS container which has a cover portion and an rim portion, a slit membrane which allows the spike of an infusion device to be inserted being inserted in the cover portion. The slit membrane is seated in the cover portion of the closure cap flush therewith.

The object underlying the invention is to provide a closure cap for a container for receiving medical liquids, and in particular a BFS container, which closure cap allows a liquid to be injected without the use of an injection needle. As well as this, it is also an object of the invention to provide a container for receiving medical liquids, and in particular a BFS container, which makes it possible for a liquid to be injected without the use of an injection needle.

These objects are achieved in accordance with the invention by virtue of the features specified in the claims. Preferred embodiments of the invention form the subject matter of the dependent claims.

The closure cap according to the invention for a container for receiving medical liquids, and in particular a BFS container for receiving an infusion solution, has a cover portion and a rim portion, an injection part for the injection of a medical liquid being arranged in the cover portion.

The injection part has an outward-pointing portion for connection having a conical recess to receive the conical tip of a needleless injection syringe while forming a seal against it, and an inward-pointing closing-off portion which has a self-sealing membrane to close off the recess in the portion for connection. The self-sealing membrane is slit and the conical tip of the injection syringe can thus be inserted easily.

It is of advantage for the closure cap according to the invention to be formed in one piece except for the self-sealing membrane. This makes it possible for the closure cap to be manufactured in large numbers at low cost.

In a preferred embodiment of the closure cap, the closing-off portion of the injection part has a recess in which the self-sealing membrane is inserted by being snapped into place. The self-sealing membrane is preferably fixed in place in the recess by an inwardly projecting rim of the closing-off portion by a clamping action. Rather than an inwardly projecting rim which extends around the entire circumference of the closing-off portion, the closing-off portion may also have hooks arranged to be distributed around the circumference to fix the self-sealing membrane in position by a clamping action.

In a further preferred embodiment of the invention, the recess in the closing-off portion has a first cylindrical section which merges with the cover portion, and a second cylindrical section which follows on from the first cylindrical section, the first cylindrical section being of a smaller inside diameter than the second cylindrical section.

A preferred embodiment of the closure cap makes provision for the self-sealing membrane to have an annular section which is arranged in the second cylindrical section of larger inside diameter of the recess, and a dished section which follows on from the annular section by way of a central web and which is arranged in the first cylindrical section of smaller inside diameter. The self-sealing membrane thus has a secure hold in the recess in the closing-off portion.

The dished section of the self-sealing membrane preferably has a bowl-like depression. The bowl-like depression on the one hand ensures that that the conical tip of the syringe is reliably guided and on the other hand guarantees that the membrane seals reliably on the conical tip being withdrawn. It has been found in tests that the special configuration of the membrane is crucial to immediate re-closure, the sealing of the membrane being further increased as the internal pressure in the pack increases.

In an embodiment which is a particular preference, the closing-off portion of the injection part having the self-sealing membrane is so designed that, when the conical tip of the injection syringe is inserted, the membrane is compressed in the axial direction in the recess. As a result, the membrane opens when the conical tip is inserted. On the one hand the self-sealing membrane is adequately fixed in place in the recess in the closing-off portion but on the other hand is so freely movable that the membrane can be compressed in the axial direction when the conical tip is inserted. The height of the membrane is reduced when this happens, i.e. the top face of the membrane loses contact with the surface of the closing-off portion against which it rests.

The closing-off portion of the injection part may be designed for a Luer syringe or a Luer-lock syringe. The portion for connection of the injection part preferably has an outside thread, thus enabling a Luer-lock connection to be made to the syringe.

To allow the self-sealing membrane to be closed aseptically, the portion for connection is preferably sealed off by a break-off part which is connected to the top end of the portion for connection via an annular zone for fracture. On the break-off part being broken off, the self-sealing membrane is exposed and the conical tip of the syringe can thus be inserted.

To improve handling, the break-off part preferably has a lateral tab for gripping which extends to the rim portion of the cover portion of the closure cap.

As well as the injection part, the closure cap according to the invention may also have a withdrawal part to allow a medical liquid to be withdrawn with a spike. The withdrawal part preferably also has an outward-pointing portion for connection having a recess into which a spike is inserted, and an inward-pointing closing-off portion which is closed off by a self-sealing membrane.

The piercable membrane is inserted in a recess in the closing-off portion of the withdrawal part by being snapped into place. The membrane is preferably fixed in place by an inwardly projecting rim of the closing-off portion by a clamping action. The closing-off portion of the withdrawal part too is preferably closed off by a break-off part which is connected to the top end of the portion for connection via an annular zone for fracture. The break-off part of the withdrawal part too preferably has a lateral tab for gripping which extends to the rim portion of the cover portion.

The container according to the invention, which is in particular an infusion or transfusion container which preferably takes the form of a bottle, is closed off by the closure cap described above.

An embodiment of the invention will be described in what follows by reference to the drawings.

BRIEF DESCRIPTION OF THE DRAWINGS/FIGURES

FIG. 5 is a view in section of the closure cap shown in FIG. 1 and

FIG. 6 shows an embodiment of container according to the invention having the closure cap according to the invention.

FIGS. 1 and 2 are side elevations of the closure cap according to the invention which has an injection part A and a withdrawal part B. Except for the self-sealing, or in other words piercable, membrane, the closure cap is a one-piece component made of plastics material which can be inexpensively manufactured in large numbers.

DETAILED DESCRIPTION OF THE INVENTION

Figure 1:
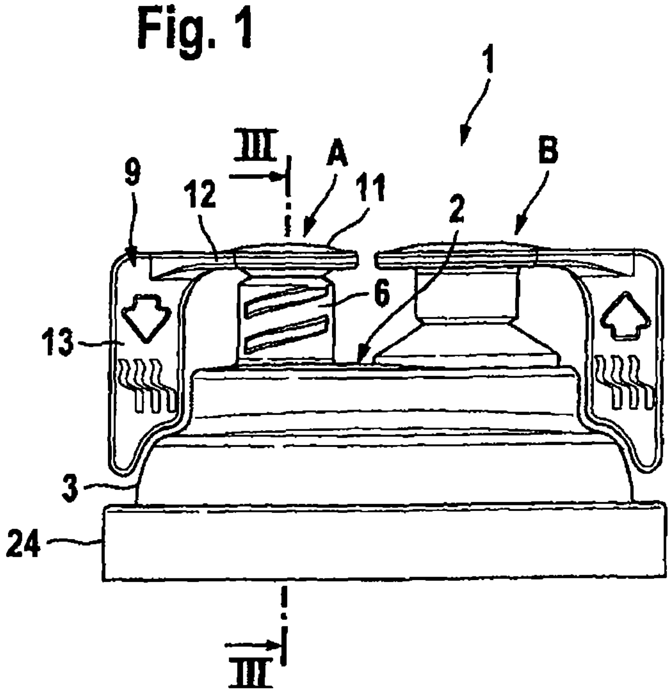
FIG. 1 shows an embodiment of closure cap according to the invention.
Figure 2:
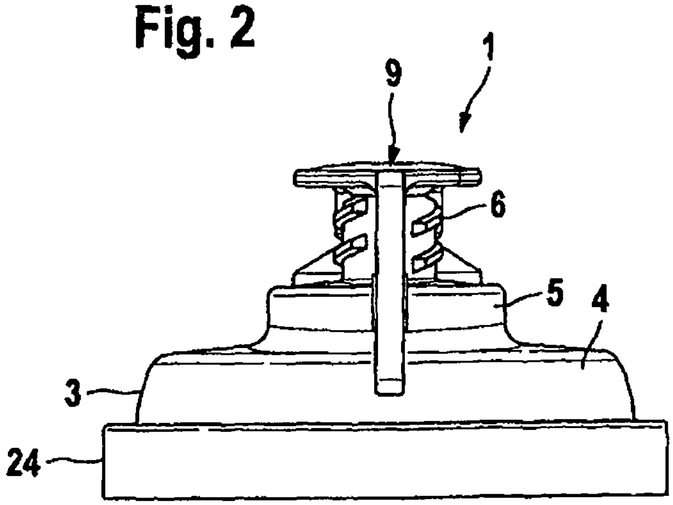
FIG. 2 is a side elevation of the closure cap shown in FIG. 1.
Figure 3:
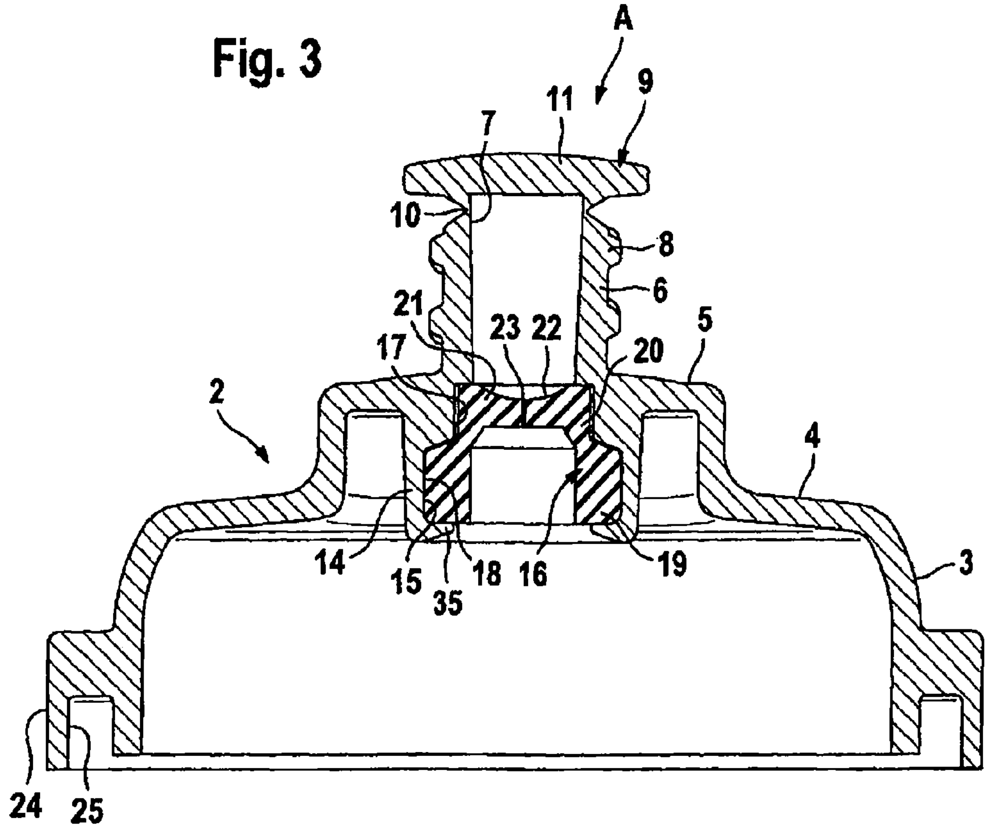
FIG. 3 is an enlarged section through the closure cap shown in FIG. 1, on line III-III.

The closure cap 1 has a cover portion 2 and a rim portion 3. The cover portion 2 has an outer section 4, and an inner section 5 which projects outwards. From the inner section 5 which projects outwards, a portion for connection 6 for the insertion of the conical tip of a needleless injection syringe points outwards (FIG. 3). The portion for connection 6 has a conical recess 7 for receiving the conical tip of the syringe while forming a seal against it, and an outside thread 8. The conical recess 7 and the outside thread 8 are so designed that a standard commercial Luer-lock syringe can be connected to the portion for connection.

The portion for connection 6 is closed off by a break-off part 9 which is connected to the top end of the portion for connection via an annular zone for fracture 10. The break-off part 9 has a round cap 11 to which a lateral tab for gripping 13, which extends downwards to the rim portion of the cover portion, is connected via a narrow bridge 12. The tab for gripping 13 is so designed that it does not extend beyond the closure cap laterally.

From the central section 5 of the cover portion 2, a closing-off portion 14, which has a recess 15, points inwards. Inserted in the recess 15 in the closing-off portion 14 is a self-sealing membrane 16 which is seated in the recess by being snapped thereinto.

The recess 15 in the closing-off portion 14 has an upper cylindrical section 17 which merges with the central section 5 of the cover portion 2. Following on from the upper cylindrical section 17 is a lower cylindrical section 18 which is of a larger inside diameter than the upper cylindrical section 17. The self-sealing membrane 16 therefore has a lower annular section 19 of a larger outside diameter, which is seated in the lower cylindrical section 18 of the recess 15. An upper, dished section 21 of a smaller outside diameter, which is seated as a close fit in the upper cylindrical section 17 of the recess 15, follows on, via a central bridge 20, from the annular section 19 of the membrane 16. The closing-off portion has an inwardly projecting rim 35 which fixes the membrane 16 in place by a clamping action. The dished section 21 of the membrane 16 has a bowl-like depression 22 which is provided with one or more slits 23 and is for example slit in a cross.

The rim portion 3 of the closure cap 1 has at the bottom a rim 24 in bead form which has, on the underside, a groove extending round in a loop. The closure cap can be fitted onto a bottle, in which case the top edge of the neck of the bottle engages in the groove 25 in the rim 24 in bead form of the closure cap.

Figure 4C:
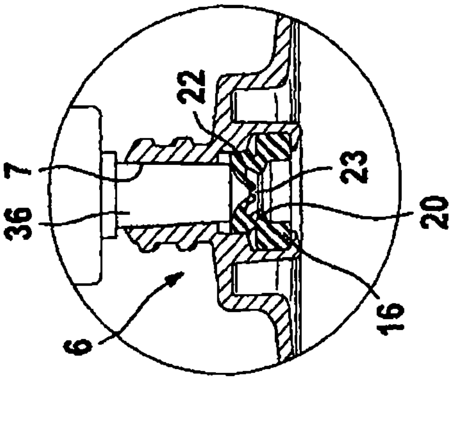
FIG. 4*c* is an enlarged view of a detail of FIG. 4*b,*
Figure 4B:
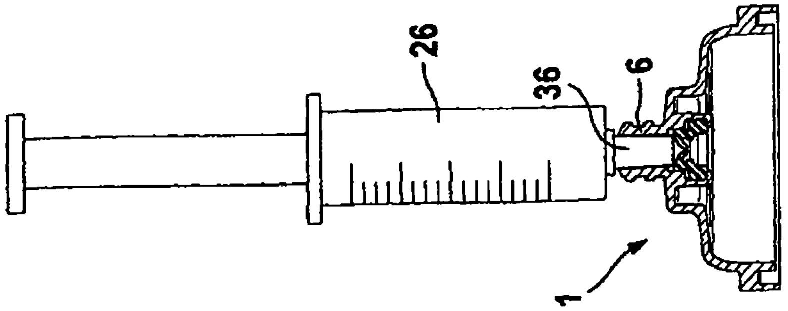
FIGS. 4*a* and 4*b* show the closure show the closure cap before and after the insertion of the conical tip of an injection syringe.
Figure 4A:
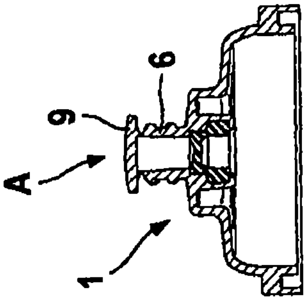

The way in which the injection part A of the closure cap operates will be described below by reference to FIGS. 4A, 4B and 4C.

To allow a liquid, such for example as a medication, to be injected with a needleless injection syringe, the break-off part 9 is first broken off the portion for connection 6 by pivoting the tab for gripping 13 sideways. This exposes the self-sealing membrane 16. The conical tip 36 of a needleless injection syringe 26 is inserted in the conical recess 7 in the portion for connection 6. When this is done, the conical tip 36 presses against the dished section 22 of the self-sealing membrane 16, as a result of which the membrane is compressed (FIG. 4C). As a result, the central bridge 20 of the membrane 16 is pressed inwards, in which case the dished section 22 is opened in the region of the slits 23. The medication can now be injected.

As well as the injection part A, the closure cap also has a withdrawal part B. The injection and withdrawal parts A, B are arranged next to one another, in the central section 5 of the cover portion 2 of the closure cap, laterally of the axis of the closure cap. The withdrawal part B is of the same construction as the injection part A (FIG. 5).

The withdrawal part B has a portion for connection 27 which points outwards from the central section 5 of the cover portion 2 and which has a recess 28 for the insertion of the spike of an infusion device. The recess 28 in the portion for connection 27 is closed off by a break-off part 29 which is connected to the top end of the portion for connection via an annular zone for fracture 30. The break-off part 30 once again has a lateral tab for gripping 31 which is of the same form as the tab for gripping of the break-off part of the injection part. From the central section 5 of the cover portion 2, a closing-off portion 32, in which a membrane 33 able to be pierced by a spike is fixed in place by a clamping action, points downwards. The membrane 33 is held in place by an inwardly projecting rim 34 of the closing-off portion 32. Once the break-off part 29 has been broken off, the membrane 33 is exposed, and is pierced by the spike. A liquid can be withdrawn with the spike.

FIG. 6 shows the closure cap according to the invention together with a container according to the invention, which in the present embodiment is a BSF bottle.

The closure cap 1 is seated firmly on the neck 37 of the bottle 38, which latter is filled with an infusion solution for example. Because the neck of the bottle is not closed off but is open in the region at the top, the liquid is in direct contact with the cap. It is thus possible for a medication to be injected with a needleless injection syringe. The closure cap preferably takes the form of a screw-cap which is screwed onto the neck 37 of the bottle. It is however also possible for the closure cap to be welded to the neck of the bottle.

What is claimed is:

1. A closure cap for a container for receiving medical liquids having a cover portion and a rim portion, comprising:

an injection part for the injection of a medical liquid being arranged in the cover portion; wherein the injection part comprises:

an injection outward-pointing portion for connection having a conical recess to receive the conical tip of a needleless injection syringe while forming a seal against it, wherein the injection outward-pointing portion for connection is sealed off by a break-off part which is connected to a top end of the injection outward-pointing portion for connection via an annular zone for fracture, the break-off part having a lateral tab for gripping which extends to the rim portion of the closure cap, and an injection inward-pointing closing-off portion which has a self-sealing membrane to close off the conical recess in the portion for connection, wherein the self-healing membrane is slit;

and a withdrawal part to allow a medical liquid to be withdrawn, wherein the withdrawal part comprises:

a withdrawal outward-pointing portion for connection having a recess for receiving a spike, and a withdrawal inward-pointing closing-off portion which has a piercable membrane for closing off the recess in the withdrawal outward-pointing connection, the closing-off portion being closed off by a break-off part which is connected to the a top end of the withdrawal outward-pointing portion for connection via an annular zone for fracture, the break-off part having a lateral tab for gripping which extends to the rim portion of the closure cap.

2. A closure cap according to claim 1, wherein the self-sealing membrane is inserted in the recess of the inward-pointing closing-off portion of the injection part by a snap fit.

3. A closure cap according to claim 2, wherein the inward-pointing closing-off portion of the injection part has an inwardly projecting rim which fixes the self-sealing membrane in place in the recess in the closing-off portion of the injection part by a clamping action.

4. A closure cap according to claim 1, wherein the inward-pointing closing-off portion of the injection part is configured to compress the self-sealing membrane in the axial direction in the recess of the injection part when the conical tip of an injection syringe is inserted, to thereby cause the membrane to be opened.

5. A closure cap according to claim 1, wherein the recess in the inward-pointing closing-off portion has a first cylindrical section which merges with the cover portion and a second cylindrical section which follows on from the first cylindrical section and which is of a larger inside diameter than the first cylindrical section.

6. A closure cap according to claim 5, wherein the self-sealing membrane has an annular section which is arranged in the second cylindrical section of the recess of the injection part, and a dished section which follows on from the annular section by way of a central web and which is arranged in the first cylindrical section.

7. A closure cap according to claim 6, wherein the dished section of the self-sealing membrane has a bowl-like depression.

8. A closure cap according to claim 1, wherein the outward-pointing connection portion of the injection part has an outside thread.

9. A closure cap according to claim 1, wherein the outward-pointing connection portion is sealed off by a break-off part which is connected to one end of the connection portion via an annular fracture zone.

10. A closure cap according to claim 1, wherein the piercable membrane in the withdrawal part is inserted in the recess of the withdrawal outward-pointing connection portion by a snap fit.

11. A closure cap according to claim 10, wherein the closing-off portion of the withdrawal part has an inwardly projecting rim which fixes the piercable membrane in place in the recess of the outward-pointing connection portion by a clamping action.

12. A closure cap of claim 1, wherein the closure cap is a blow-fill-seal (BFS) container.

* * * * *